United States Patent [19]

Kantor

[11] 4,108,147

[45] Aug. 22, 1978

[54] DIRECT CONTACT MICROWAVE DIATHERMY APPLICATOR

[75] Inventor: Gideon Kantor, Garrett Park, Md.

[73] Assignee: The United States of America as represented by the Department of Health, Education and Welfare, Washington, D.C.

[21] Appl. No.: 737,590

[22] Filed: Nov. 1, 1976

[51] Int. Cl.² ............................................. A61N 5/02
[52] U.S. Cl. ............................. 128/404; 219/10.55 A
[58] Field of Search ....................... 128/404, 405, 413; 219/10.55 R, 10.55 A, 10.55 D, 10.55 F, 10.55 M, 10.57, 10.81; 343/772, 782, 783, 785

[56] References Cited

U.S. PATENT DOCUMENTS

| | | | |
|---|---|---|---|
| 2,407,690 | 9/1946 | Southworth | 128/422 |
| 2,480,682 | 8/1949 | Stiefel | 219/10.55 R |
| 2,718,580 | 9/1955 | Shirley | 219/10.55 R |
| 2,943,174 | 6/1960 | Parker | 219/10.55 R X |
| 3,457,385 | 7/1969 | Cumming | 219/10.55 A X |

Primary Examiner—William E. Kamm
Attorney, Agent, or Firm—Browdy & Neimark

[57] ABSTRACT

A direct contact microwave diathermy applicator consisting of a rectangular waveguide in which are secured two parallel Teflon dielectric loading slabs. This assembly is secured in a waveguide-coaxial cable adaptor, enabling the applicator to be energized from a microwave diathermy machine. The configuration of the applicator causes the tissue under treatment to exhibit approximately uniform heating patterns over a substantial portion of the treated tissue area and minimizes harmful scatter radiation. This uniform heating is particularly useful in effecting microwave induced hyperthermia treatment of cancer.

10 Claims, 6 Drawing Figures

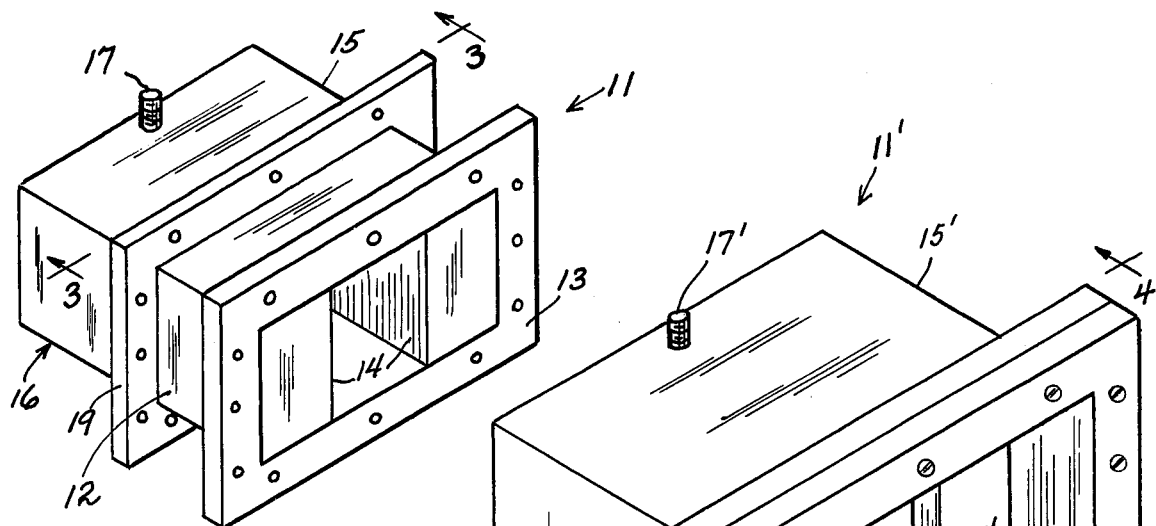
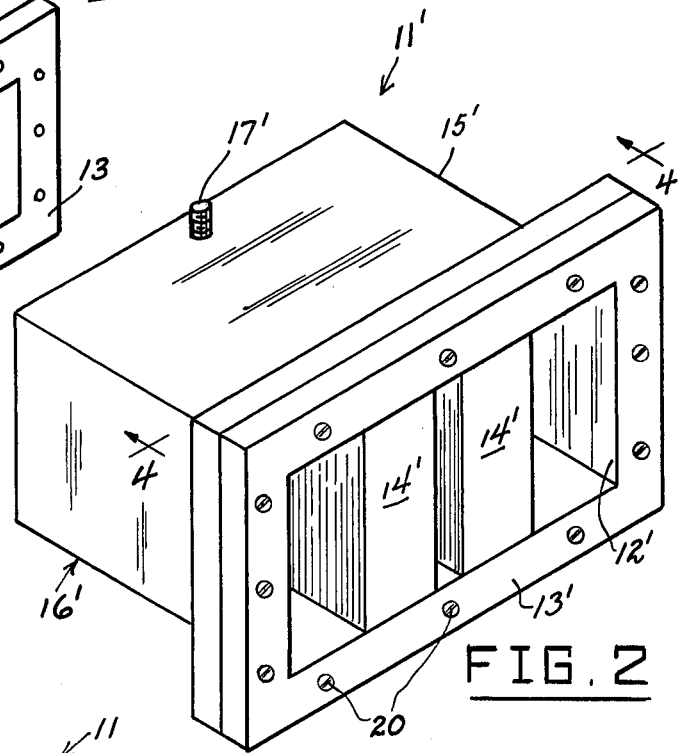
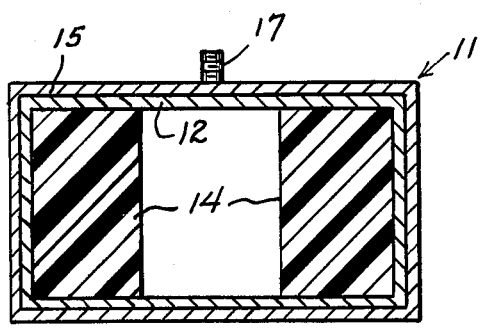
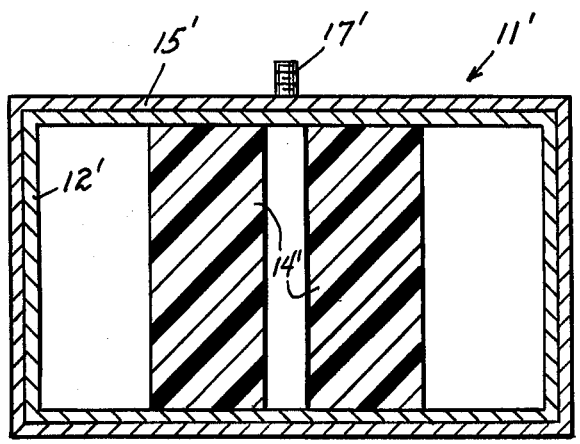
FIG. 1
FIG. 2
FIG. 3
FIG. 4

DIRECT CONTACT MICROWAVE DIATHERMY APPLICATOR

FIELD OF THE INVENTION

This invention relates to electrotherapeutic apparatus, and more particularly to direct-contact applicators for use with mocrowave diathermy machines.

BACKGROUND OF THE INVENTION

According to existing practice of diathermy therapy at the 2.45 GHz band, only spaced external applicators are used for radiating the tissue under treatment. Since the applicator is spaced from the patient's tissue, the radiated energy is not confined to the prescribed tissue area but also irradiates uprescribed tissue of the patient, as well as the operator and other persons in the vicinity of the diathermy machine, causing the possibility of exposing the operator and other persons from exposure to the hazardous levels of energy fields.

SUMMARY OF THE INVENTION

Accordingly, a main object of the present invention is to overcome the disadvantages of spaced applicators, namely, to avoid the possibilities of unintended overexposures by eliminating the scatter of energy by employing applicators which can be placed in direct contact with the tissue to be treated and which confines the radiation substantially to the intended tissue area.

A further object of the invention is to provide direct-contact microwave diathermy applicators which provide a more uniform heating pattern than do the presently available spaced applicators. Such a heating pattern is for example needed for microwave induced hyperthermia treatments of cancer because there is a critical temperature above which both cancer and healthy tissues are killed. In a temperature region below this critical temperature, cancer tissue responds to treatment while healthy tissue is not affected.

A still further object of the invention is to provide an improved direct-contact microwave diathermy applicator which employs an inhomogeneously filled wave guide, which overcomes the disadvantages of spaced applicators, and which eliminates the scatter of energy, while providing a more uniform heating pattern than that obtained from a spaced applicator of the type presently available, the improved applicator being of relatively simple construction, being easy to use, and preventing unintended radiation exposure of external tissue areas and to the operator and other persons in the vicinity of the associated diathermy machine.

A still further object of the invention is to provide an improved direct-contact microwave diathermy applicator for use in the 2.45 GHz diathermy irradiation band which employs a loading waveguide containing Teflon slabs which fit tightly in the waveguide and which are arranged to provide a substantially uniform temperature distribution at the center of the resultant heating pattern, the applicator operating with minimum scatter radiation and being physically easy to manipulate.

BRIEF DESCRIPTION OF THE DRAWINGS

Further objects and advantages of the invention will become apparent from the following description and claims, and from the accompanying drawings, wherein:

FIG. 1 is a perspective view of a typical improved microwave diathermy applicator assembly according to the present invention, shown with the main applicator portion partly received its associated waveguide-coaxial cable adaptor.

FIG. 2 is a perspective view of another form of microwave diathermy applicator assembly according to the present invention, shown fully assembled.

FIG. 3 is an enlarged vertical cross-sectional view taken substantially on line 3—3 of FIG. 1.

FIG. 4 is an enlarged vertical cross-sectional view taken substantially on line 4—4 of FIG. 2.

DESCRIPTION OF PREFERRED EMBODIMENTS

Figure 5:
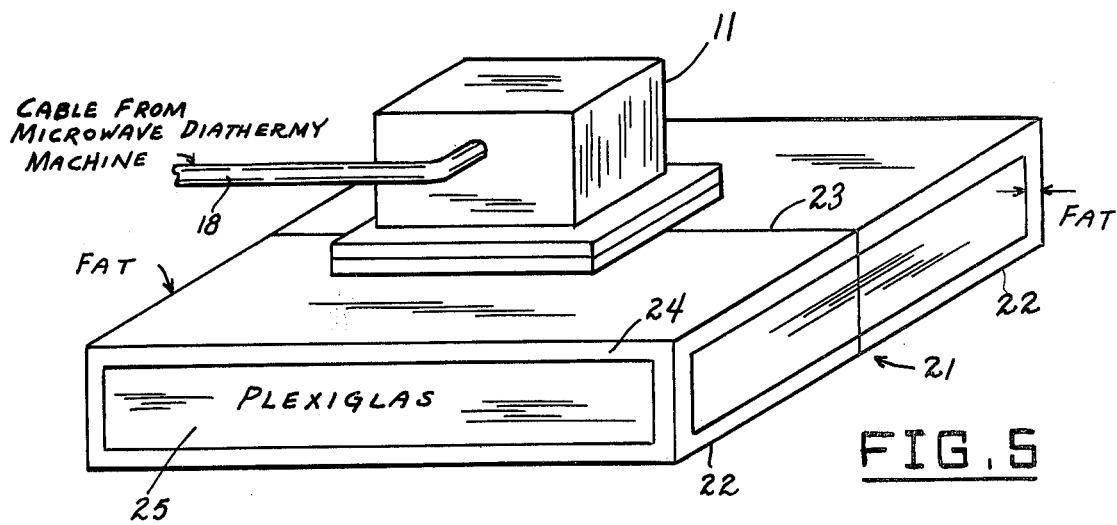
FIG. 5 is a perspective view showing how a typical direct-contact microwave diathermy applicator according to the present invention may be tested, using a fat-skin planar phantom of simulated tissue.

Referring to the drawings, and particularly to FIG. 1, 11 generally designates a typical microwave diathermy applicator assembly according to the present invention, for direct application at the 2.45 diathermy irradiation band. The main portion of the applicator 11 comprises a rectangular waveguide member 12 provided with a front peripheral securing flange 13. Tightly engaged in the opposite side portions of waveguide member 12 are respective polytetrafluoroethylene (Teflon) slabs 14, 14, whose front ends are substantially flush with the plane of flange 13. A specified width of slab 14 is necessary to sustain a uniform electromagnetic wave, the transverse electromagnetic mode (TEM), in the air space between the two slabs as noted below.

In a typical small size applicator according to FIG. 1, the waveguide section 12 is 3 inches long and has an inside cross-section 4.3 inches wide and 2.15 inches high. The Teflon slabs 14, 14 are 3 inches long and 1.26 inches wide. For a medium size applicator, the waveguide section 12 is also 3 inches long, and has an inside cross-section 5.1 inches wide and 2.55 inches high, the Teflon slabs 14, 14 being also 3 inches long and 1.26 inches wide. In each case the slabs are of a height sufficient to fit tightly in the opposite side portions of the waveguide cavity.

The waveguide section 12 is closely receivable in the rectangular body 15 of a waveguide-coaxial adaptor 16 provided with a connection terminal 17 for connecting the applicator to the end of a coaxial cable 18 (see FIG. 5) leading to the output of a 2.45 GHz microwave diathermy machine. The above connection terminal 17 must be placed symmetrically with respect to the vertical walls of the rectangular body 15 to prevent excitation of the first order asymmetric Longitudinal Section Electric (LSE) mode which would induce a less uniform heating pattern. The front end of body 15 is provided with a peripheral flange 19. The flanges 13 and 19 have registering apertures for receiving fastening screws or bolts to secure the flanges in abutting relationship.

The spaced Teflon slabs 14, 14 serve as loading and absorption elements to modify the heating action of the applicator, applied directly to a tissue area to be treated, so as to provide a desirable heating pattern, for example, a pattern wherein the temperature is substantially uniform at its central portion. The slabs 14 must be spaced sufficiently close to each other, as is this case in this disclosure, to prevent the excitation of the second higher order LSE mode in the air space between them which would induce a less uniform heating pattern.

FIG. 2 shows a large size direct-contact microwave diathermy applicator according to the present invention, designated generally at 11'. In this embodiment, the main portion of the applicator comprises a rectangular waveguide member 12' provided with a front peripheral flange 13'. Tightly fitted in the intermediate portion of member 12', coextensive in length therewith, are the spaced longitudinally extending Teflon slabs 14', 14' whose front ends are substantially flush with the plane of flange 13'. A specified width of slabs 14' is necessary to sustain a TEM mode in the air space between the two slabs as noted below. The waveguide section 12' is closely received in the rectangular body 15' of a waveguide-coaxial cable adaptor 16' provided with a terminal 17' for connecting the applicator to a coaxial feed cable 18 leading from the output of a 2.45 GHz microwave diathermy machine. The above connection terminal 17' must be placed symmetrically with respect to the vertical walls of the rectangular body 15' to prevent excitation of the first order symmetric LSE mode. The front end of body 15' is provided with a peripheral flange 19' which is secured to flange 13' by suitable screws or bolts 20, as shown in FIG. 2.

In a typical embodiment, following the showing in FIG. 2, the waveguide section 12' is 3 inches long and has an inside cross-section 6.5 inches wide and 3.25 inches high. The Teflon slabs 14', 14' are 3 inches long and 1.26 inches wide. The spacing between the slabs 14', 14' at the midportion of the waveguide cavity is $\frac{1}{2}$ inch. The slabs 14', 14' are of a height to fit tightly in the intermediate portion of the waveguide cavity. The slabs 14' must be spaced sufficiently close to each other, as is the case in this disclosure, to prevent the excitation of the second higher order LSE mode in the air space between them which would induce a less uniform heating pattern.

As in the embodiment of FIG. 1, the Teflon slabs 14', 14' serve as loading and absorption elements to modify the heating action of the directly-applied applicator so as to provide a desirable heating pattern, namely, wherein the temperature is substantially uniform over the central portion due to the TEM excitation in the air space between the two slabs 14'.

Figure 6:
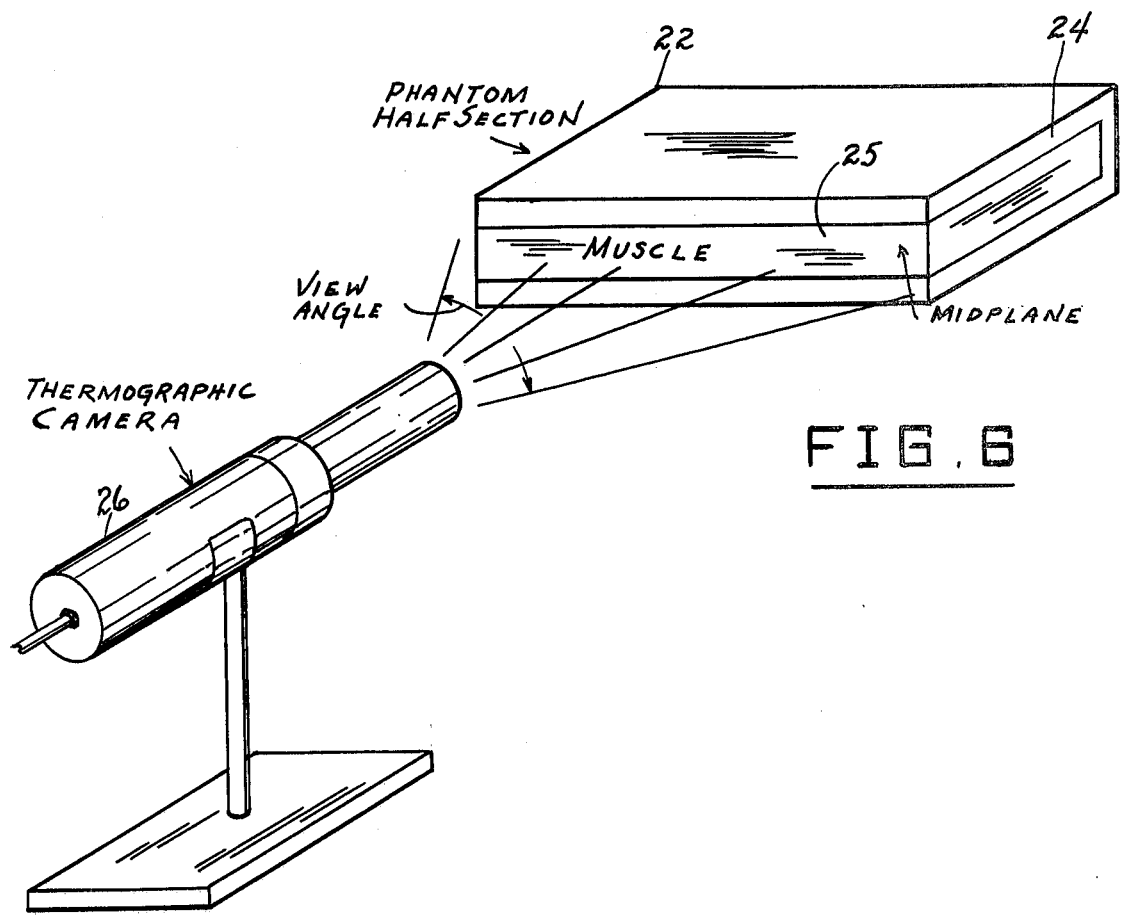
FIG. 6 is a perspective view showing how a thermographic camera may be employed to obtain a scanning readout of the temperature distribution at the center of the heating pattern in the midplane of a simulated-tissue phantom such as that employed in FIG. 5.

In testing the performance of an applicator 11 or 11', a fat-skin planar phantom 21 (see FIG. 5) may be used to stimulate tissue to be treated. The phantom 21 may comprise a pair of symmetrically-mating blocks 22, 22, abutting at a vertical midplane, as shown at 23 in FIG. 5. Each block has an outer layer 24 of a material having microwave absorption or dielectric characteristics similar to fat and an inside layer similar to muscle, such as described in A. W. Guy, J. F. Lehmann, J. A. McGougal and C. C. Sorensen, "Studies on Therapeutic Heating by Electromagnetic Energy", page 31, "Thermal Problems in Biotechnology", American Society of Mechanical Engineers, N.Y., 1965; the fat material consists of 84.81% Laminac Polyester Resin, 0.45% Catylist (Methyl Ethyl Ketone Peroxide "60%"), 0.24% Acetylene black and 14.5% aluminum powder; the muscle material consists of 15.2% Powdered Polyethylene, 76.4% Saline Solution (12 gms salt/liter) and 8.4% Silly "Stuff" (Silly Stuff from Whamo Co. California.) Each block also has an inner matrix 25 simulating muscle. The testing procedure comprises first heating the abutting blocks 22, 22, arranged as in FIG. 5, with a direct contact applicator 11 or 11' placed thereon over the abutment midplane at 23. The power output of the microwave diathermy machine, operating at 2.45 GHz, is about 130 watts, lasting for 5 seconds. The resultant temperature distribution at the center of the heating pattern in the midplane of the phantom is measured by using a thermographic camera 26 (see FIG. 6). The camera scanning line is set parallel to the fatmuscle interface of the planar phantom. For the small direct contact applicator of FIG. 1, in a typical test, the central portion of the heating pattern, about 1.6 inches in length, showed an average temperature rise of 2.7° C, with limits of ± 0.2° C; for the medium size direct-contact applicator 11 above described, the central portion, about 2.9 inches in length, showed an average temperature rise of 1.2° C, with limits of ± 0.2° C, and for the large direct-contact applicator 11' of FIG. 2, the central portion, about 1.85 inches in length, showed an average temperature rise of 0.8° C, with limits of ± 0.2° C.

A choice of uniform heating patterns of different sizes with different temperature distributions is for example needed in microwave induced hyperthermia treatment of cancer because cancer therapy requires heating of the entire diseased treatment area above a particular elevated temperature to prevent the spread of cancer to other tissue.

While certain specific embodiments of improved direct-contact microwave diathermy applicators have been disclosed in the foregoing description, it will be understood that various modifications within the scope of the invention may occur to those skilled in the art. Therefore it is intended that adaptions and modifications should and are intended to be comprehended within the meaning and range of equivalents of the disclosed embodiments. For example, materials which act in a manner equivalent to polytetrafluoroethylene (Teflon) in the present environment may be used in its place.

What is claimed is:

1. A direct contact microwave diathermy applicator comprising a waveguide defining a cavity and having an open front end and vertical walls, a pair of spaced-apart, parallel, tetrafluoroethylene dielectric loading slabs secured in said cavity of said waveguide and extending lengthwise toward said open front end, and means including a connecting terminal positioned substantially symmetrically to connect said waveguide to the output of a microwave diathermy machine, whereby wave propagation is effected in the TEM mode and substantially uniform heating can be effected.

2. The microwave diathermy applicator of claim 1, wherein front ends of said slabs are substantially flush with said open front end of said waveguide.

3. The microwave diathermy applicator of claim 2, wherein said spaced parallel slabs are secured in said waveguide substantially symmetrically relative to a longitudinal central plane of said waveguide.

4. The microwave diathermy applicator of claim 3, wherein said waveguide is substantially rectangular in shape and said slabs are substantially rectangular and are tightly fitted in said cavity of said waveguide.

5. The microwave diathermy applicator of claim 3, wherein said connecting means includes a sleeve-like member closely receiving said waveguide and being provided with said connecting terminal consisting of an outwardly extending terminal adapted to be connected to a coaxial cable leading to the output of the microwave diathermy machine.

6. The microwave diathermy applicator of claim 5, and wherein said waveguide and sleeve-like member are provided with abutting front peripheral flanges.

7. The microwave diathermy applicator of claim 6, and fastening means connecting said abutting peripheral flanges.

8. The microwave diathermy applicator of claim 1, and wherein the front ends of said slabs are substantially flush with the open front end of said waveguide and are secured in the waveguide substantially symmetrically relative to a longitudinal central plane of the waveguide, and wherein said slabs are spaced apart by a distance less than 2.6 inches.

9. The microwave diathermy applicator of claim 8, and wherein said slabs are located in the opposite side end portions of the waveguide cavity.

10. The microwave diathermy applicator of claim 8, and wherein said slabs are located in the intermediate portion of the wavegude cavity and are spaced apart by approximately ½ inch.

* * * * *

UNITED STATES PATENT AND TRADEMARK OFFICE
CERTIFICATE OF CORRECTION

PATENT NO. : 4,108,147
DATED : August 22, 1978
INVENTOR(S) : Gideon KANTOR

It is certified that error appears in the above-identified patent and that said Letters Patent are hereby corrected as shown below:

Column 1, line 19, delete "from exposure"

Column 3, line 45, after "portion" insert --of the pattern--

Signed and Sealed this

Third Day of April 1979

[SEAL]

Attest:

RUTH C. MASON
Attesting Officer

DONALD W. BANNER
Commissioner of Patents and Trademarks